United States Patent [19]

Jisander

[11] Patent Number: 5,769,898
[45] Date of Patent: Jun. 23, 1998

[54] DEVICE FOR SUPPORTING A MEMBRANE USED FOR PROMOTING BONE GROWTH

[75] Inventor: Sven Jisander, Bjärred, Sweden

[73] Assignee: Nobel Biocare AB, Gothenburg, Sweden

[21] Appl. No.: 725,900

[22] Filed: Oct. 4, 1996

Related U.S. Application Data

[63] Continuation of Ser. No. 341,196, Dec. 5, 1994, abandoned.

[30] Foreign Application Priority Data

Dec. 9, 1993 [SE] Sweden ............................. 93.04093-9

[51] Int. Cl.[6] .............................. A61F 2/28; A61B 17/84
[52] U.S. Cl. ................................ 623/16; 606/72; 433/173
[58] Field of Search ........................ 623/16, 18; 433/173, 433/201.1; 606/72, 74

[56] References Cited

U.S. PATENT DOCUMENTS

| | | | |
|---|---|---|---|
| Re. 34,632 | 6/1994 | Berggren et al. ........................ | 623/18 |
| 4,292,693 | 10/1981 | Shea et al. ............................ | 623/16 X |
| 4,404,692 | 9/1983 | Eftekhar ................................ | 623/18 X |
| 4,728,331 | 3/1988 | Russier ................................... | 623/16 |
| 4,889,110 | 12/1989 | Galline et al. ............................ | 606/69 |
| 4,959,072 | 9/1990 | Morslcher ................................. | 623/22 |
| 4,976,728 | 12/1990 | Willert et al. ............................. | 623/22 |
| 5,002,579 | 3/1991 | Copf et al. ................................ | 623/23 |
| 5,032,129 | 7/1991 | Kurze et al. .............................. | 623/16 |
| 5,035,714 | 7/1991 | Willert et al. ............................. | 623/16 |
| 5,052,930 | 10/1991 | Lodde et al. ............................. | 433/173 |
| 5,092,889 | 3/1992 | Campbell ................................. | 623/16 |
| 5,092,894 | 3/1992 | Kenny ...................................... | 623/18 |
| 5,306,149 | 4/1994 | Schmid et al. ........................... | 433/173 |

FOREIGN PATENT DOCUMENTS

| | | | |
|---|---|---|---|
| 0019062 | 3/1980 | European Pat. Off. ................. | 606/74 |
| 1145979 | 11/1957 | France .................................. | 433/173 |
| 3732128 | 4/1989 | Germany .............................. | 433/173 |
| 4223 153 A1 | 1/1993 | Germany . | |
| 405-064646 | 3/1993 | Japan .................................. | 433/201.1 |
| 679 117 A5 | 12/1991 | Switzerland . | |
| 0606239 | 11/1985 | U.S.S.R. .................................. | 623/16 |
| 1489750 | 6/1989 | U.S.S.R. .................................. | 606/72 |
| WO91/14404 | 10/1991 | WIPO . | |

OTHER PUBLICATIONS

"Generation of New Bone Around Titanium Implants Using a Membrane Technique," The Int. Journal of Oral & Maxillofacial Implants, vol. 4, No. 1, 1989, pp. 19–25.

Gore-Tex Augmentation Material. c 1991 by W. L. Gore & Associates Inc. Sep. 1991.

*Primary Examiner*—David H. Willse
*Attorney, Agent, or Firm*—Law Offices Pollock, Vande Sande & Priddy

[57] ABSTRACT

A device for supporting a flexible, biocompatible membrane of the type which is arranged between the soft tissue and the bone tissue of a human or an animal so that a space is formed between the membrane and the bone tissue for the purpose of establishing bone growth in this space comprises a central annular part for connection to an implant which is anchored in the bone tissue, and a peripheral part which is intended to extend outwardly form the central part over the space in which bone growth is sought and to form a support for the flexible membrane. The peripheral part consists of one or more wire loops, the wire being made of a biocompatible material, preferably titanium, and being easily bendable by hand and shortened if necessary upon application, while being sufficiently stiff to maintain its shape after bending. The device can also be used in conjunction with bone transplants, the transplant being held in place, during the incorporation period, by the peripheral wire loop which is bent over the transplant and clamps the latter securely against the existing bone tissue. It is therefore possible to dispense with the screws or pins previously used for the fixing.

11 Claims, 4 Drawing Sheets

DEVICE FOR SUPPORTING A MEMBRANE USED FOR PROMOTING BONE GROWTH

This application is a Continuation of U.S. patent application Ser. No. 08/341,196, filed Dec. 5, 1994, now abandoned.

BACKGROUND OF THE INVENTION

The present invention relates to a device for promoting bone growth in connection with an implant anchored in the bone tissue, for example in the jaw bone.

The device comprises a central part for connection to the implant, and a peripheral part intended to extend out over the area where bone growth is sought and to form a support either for a flexible, biocompatible membrane of the type which is arranged between the soft tissue and the bone tissue or for a bone transplant applied in connection with the implant.

A growth of bone tissue is especially desirable in those cases where the jaw bone has been resorbed to such a great extent that the existing bone volume is too small to allow the use of releasable or firmly anchored dental prostheses. In the case of dental bridges anchored in the jaw bone, a certain minimum bone volume must be left in order to permit sufficient anchoring of a number of fixtures in the bone tissue.

It is already known to regenerate bone tissue by forming between the soft tissue and the bone tissue a space in which bone tissue can then grow freely. In the case where bone growth is sought in connection with a fixture, the space can be formed for example by mounting a dimensionally stable, cap-shaped element on the fixture so that its peripheral part extends out over an area around the fixture. A device of this type is described in SE 468 339.

Another method for creating good conditions for bone growth is to place a flexible membrane of the GORE-TEX type over the area where the bone needs to be strengthened. Also in this case too the membrane is placed between the bone tissue and the soft tissue, i.e. the gingival connective tissue, so that a space is formed between the tissues and so that the connective tissue is prevented from growing into the space. The GORE-TEX membrane consists of a porous polytetrafluoroethylene material (e-PTFE) which has been shown to have good biocompatibility and a microstructure which allows gas to penetrate through the membrane but which prevents undesired growth of cells through the membrane. The membrane technique is described for example in Generation of New Bone Around Titanium Implants Using a Membrane Technique. The Int. Journal of Oral & Maxillofacial Implants, Vol. 4, No. 1, 1989, p. 19–25, and GORE-TEX Augmentation Material. c 1991 by W. L. GORE & Associates Inc. September 1991.

By virtue of its flexibility, the membrane is easy to connect round the defective area. In order to be able to maintain a space (volume) for bone growth, the central part of the membrane is preferably made of a slightly stiffer and more dimensionally stable material. However, there is a risk that even this central part will collapse under the pressure from the surrounding connective tissue, and it is therefore already known to provide the membrane with some form of support against which the membrane can bear and/or be fixed. The support is then preferably mounted on an implant and has a peripheral part which extends out from the implant over the defective area, and the membrane is then placed over, and covers, the support. An example of a support device of this type is shown in DE 4 223 153. The support device there consists of a pyramid-like construction which is probably difficult to manufacture and difficult to adapt to the actual conditions.

SUMMARY OF THE INVENTION.

An object of this invention is to provide a membrane support which is easy to manufacture and easy to adapt to different conditions, for example the size and situation of the defective area where bone growth is wanted.

It is also already known to regenerate resorbed bone by transplantation of bone tissue. This method is used primarily in cases where the existing bone has been resorbed to such a great extent that it is difficult, with the membrane technique, to create a sufficiently large free space for bone growth. Instead, a bone transplant, for example from the patient's chin, can then be applied on the existing defective bone tissue and allowed to become incorporated thereon. The bone transplant is in this case fixed to the existing bone by means of small pins or screws, which means that it is a relatively difficult operation to perform.

A further object of the invention is therefore to provide a device which can also be used in conjunction with bone transplants and which can facilitate the fixing of the transplant to the defective bone.

The invention is characterized in that the peripheral part of the support consists of one or more wire loops in which the wire is made of a biocompatible material, preferably titanium, and can easily be bent and shortened upon application, but which is stiff enough to maintain its shape after bending.

In conjunction with a membrane, the peripheral wire loop will thus come to form a support and base for the membrane and will in this way maintain a space between the membrane and the bone tissue in order to permit bone growth in this space.

In conjunction with a bone transplant, the peripheral wire loop can easily be bent downwards over the transplant and, since it maintains its shape after bending, it can also hold the transplant in place during the incorporation period, without the transplant having to be fixed by means of screws or the like.

The accompanying drawings show a few examples of how the present invention can be realized:

DETAILED DESCRIPTION OF THE PREFERRED EMBODIMENT(s)

Figure 1:
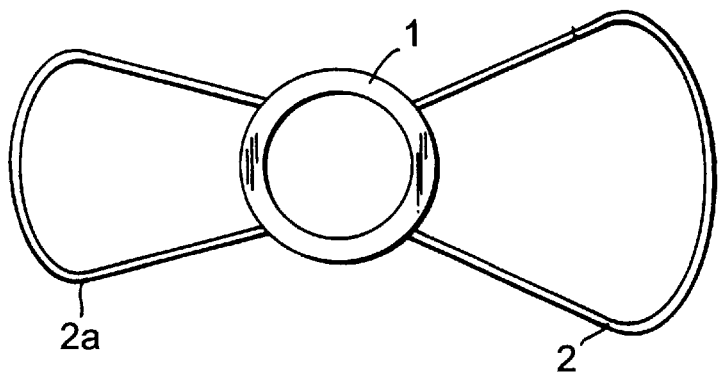
FIG. 1 shows a first embodiment of the present invention embodiment from above.
Figure 1:
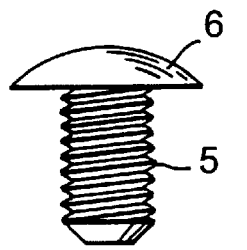
Figure 2:
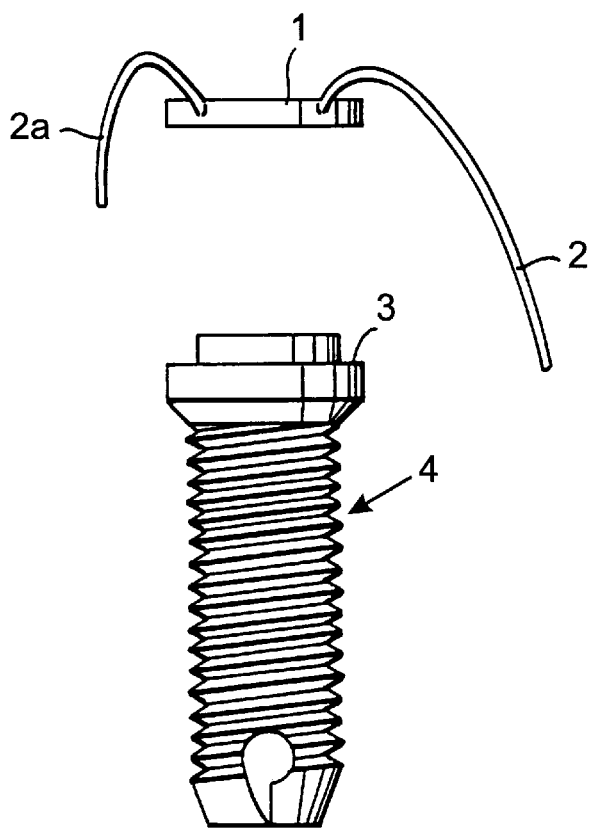
FIG. 2 shows the same variant from the side, together with an implant and a locking screw, and after the wire loops have been bent and adapted to the area in which bone growth is sought.

In accordance with FIG. 1, the device comprises a central part in the form of a ring or sleeve 1 which is intended to be placed on the flange 3 of a fixture 4, see FIG. 2. The device furthermore comprises a peripheral part in the form of two opposite loops 2, 2a which extend in a fan shape out from the central part. The loops consist of a 0.5 mm thick titanium wire which can easily be bent but which is sufficiently stiff to maintain its shape after it has been bent, i.e. plastically deformable. The ends of the wire loops are welded firmly onto the ring 1. The wire loops can advantageously be asymmetrical, so that one loop is larger than the other in its basic shape.

FIG. 2 shows a side view in which the two loops have been bent and have been adapted to the actual conditions of an implant (fixture 4) anchored in the jaw bone. One loop has been shortened in this case, since bone growth is mainly sought on only one side of the implant. FIG. 2 also shows a locking screw 5 which has a flat, rounded head 6 and which is screwed down into the internal thread of the fixture and locks the support device in the correct position.

Figure 3:
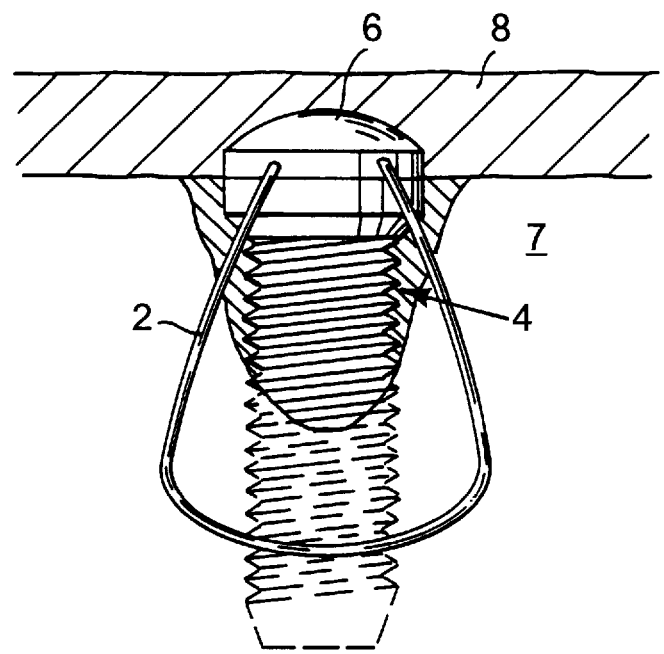
FIG. 3 shows the present device applied on the implant.

FIG. 3 shows the device mounted on a fixture 4 anchored in the jaw bone 7 and covered by soft tissue 8. In this case the bone has been resorbed around the upper part of the fixture so that the thread has been exposed, This means that the fixture has become insufficiently anchored and that there is a risk of its becoming loose under loading.

Figure 4:
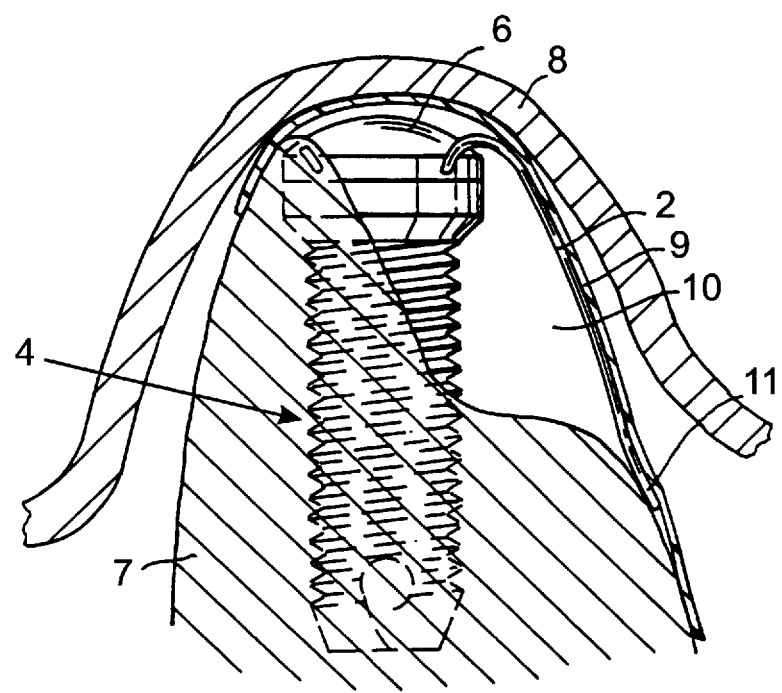
FIG. 4 shows a side view of the device together with a membrane during the period of bone incorporation.

FIG. 4 shows a side view of the conditions prevailing in the case of an insufficiently anchored fixture. A considerable part of the outer thread of the fixture is exposed since the jaw bone is too narrow in this area. With the aid of the support device and a membrane 9, a space 10 is created in which bone growth can be established.

The operation proceeds in the following way. The soft tissue 8 is first incised and folded back so that the jaw bone is exposed. The fixture is then anchored in the bone tissue in the conventional manner, and the support device is mounted on the flange of the fixture with the aid of the locking screw 6. Since only one side of the fixture is exposed and requires additional bone tissue for secure anchoring, the one loop is cut off completely, while the other loop 2 is shaped by hand to the space which is to be strengthened. The wire is bent so that its outer peripheral part 11 bears against the bone and so that a free space 10 is formed under the wire loop 2. If the original wire loop 2 is too large, it too can be cut and shortened, after which the free ends are joined together, for example knotted or twisted together.

When the support device is in place and has been fixed by means of the locking screw 6, the flexible membrane 9 of GORE-TEX is applied over the space 10. Membranes of this type are already known on the market, see above, and will therefore not be described further here. When the soft tissue 8 is replaced and stitched together, the membrane prevents soft tissue from growing into the space 10, and at the same time the support device prevents the membrane from being pressed into the space. During an incorporation period of a few months, the space 10 is instead filled with new bone tissue. At the end of this period an incision is once again made in the soft tissue 8, and the locking screw 6 is exposed and removed, after which a spacer screw is secured in a conventional manner on the fixture, and fitting of the dental prosthesis is begun.

In the example which has been described hereinabove, a 0.5 mm thick titanium wire is used. The wire preferably has a circular cross-section, but it will be understood that wires with other cross-sections can also be used, for example band-shaped wires. The wire thickness of 0.5 mm has been chosen because this thickness has been found to be suitable for making the wire such that it can easily be bent by hand and easily cut, while nevertheless being sufficiently stiff to be able to support and hold up the membrane.

Figure 5:
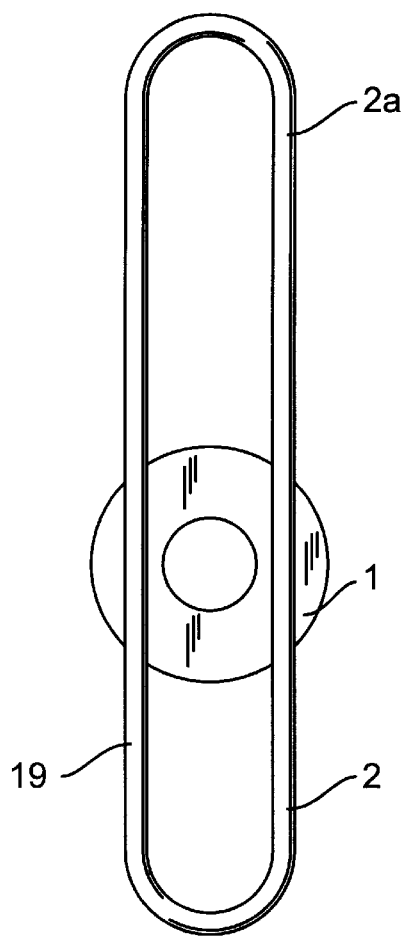
FIG. 5 shows a second embodiment of the invention from above.

FIG. 5 shows a second embodiment of the invention which also comprises an annular central part 1 and a peripheral part in the form of a closed wire loop which, with a larger loop part 2a and a smaller loop part 2, extends out from the central part 1 and can easily be bent and shaped by hand.

Figure 6:
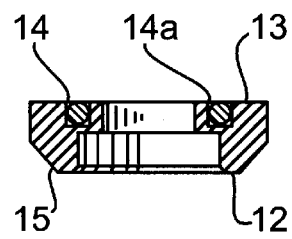
FIG. 6 shows a cross-section through the central part of this second embodiment.

As can be seen from FIG. 6, which shows a cross-section through the central part 1, the latter comprises a lower end surface 12 which is intended to bear against the flange 3 of the implant, and an upper end surface 13 which is directed away from the flange and which comprises two parallel grooves 14, 14a in which the wire loop has been fixed by means of press-fitting or has been welded. In this case the loops are made of a single closed loop which has been pressed down into the two grooves so that two part loops 2, 2a extend out from the central area. Also in this case the support device is locked to the fixture by means of a locking screw similar to the one shown in FIG. 2, the grooves with the wire being covered by the head of the locking screw during the period of incorporation. For manufacturing reasons, and in order to provide room for the grooves on the upper side, the central annular part has a diameter which slightly exceeds the diameter of the flange. That part of the central area which connects with the fixture therefore has a downwardly narrowing conical part 15.

Figure 7:
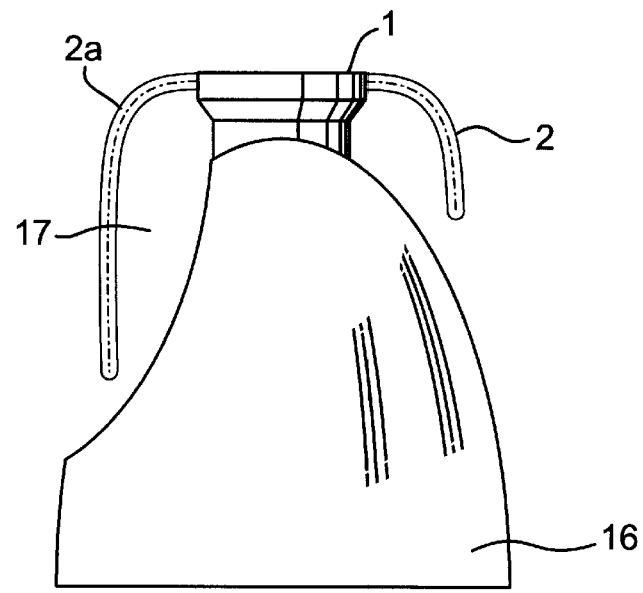
FIG. 7 shows how it has been applied on an implant.

FIG. 7 shows the second embodiment of the invention applied on an implant which is anchored in a partially resorbed jaw bone 16. The two part loops of the titanium wire have been bent so that a space 17 is formed under the support device, in which space it is possible for bone growth to take place. The membrane (not shown) is then laid on top of the support device and prevents soft tissue from penetrating into this space.

Figure 8:
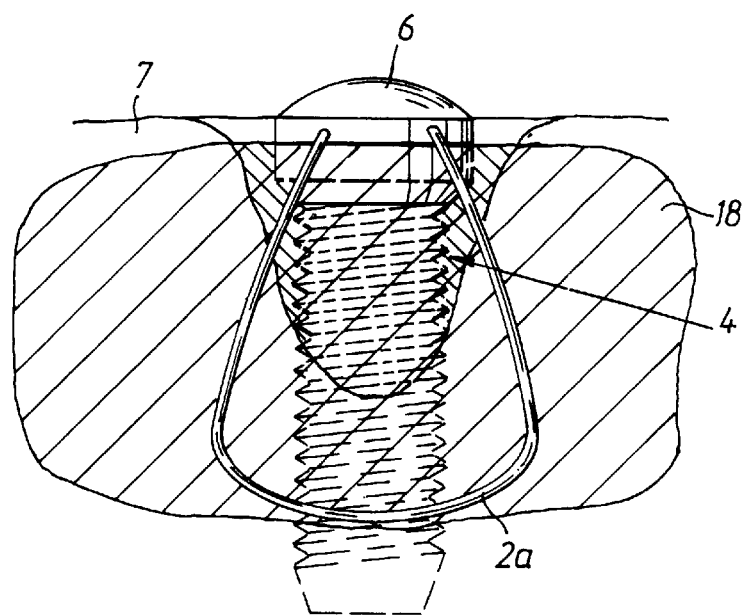
FIG. 8 shows the invention in conjunction with a bone transplant which is applied in connection with a fixture.
Figure 9:
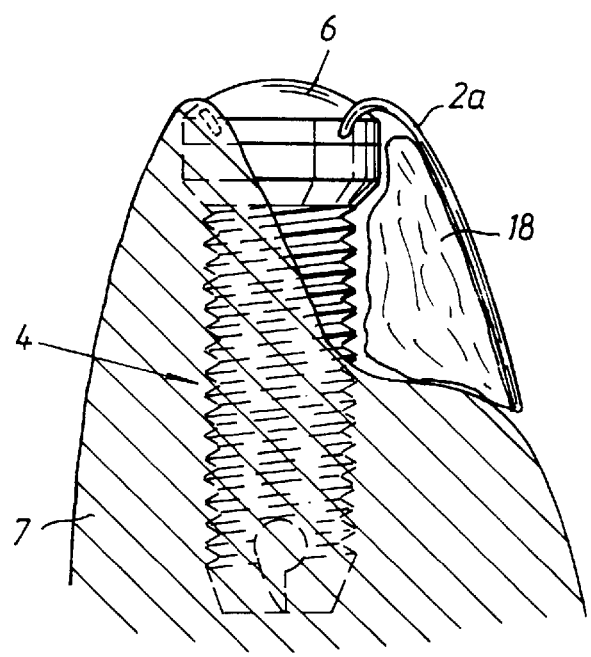
FIG. 9 shows the same application, but at right angles in relation to FIG. 8.

FIG. 8 shows an application of the invention in which the membrane technique is not used, but instead a bone transplant 18 from, for example, the patient's chin. The transplant is applied in connection with a fixture 4 in the area where bone formation is required. Bone transplantation is already known and is therefore not described in further detail here. As was mentioned in the introduction, transplants have previously been fixed on the existing bone tissue by means of pins or screws so as to hold them in place during the period of incorporation. According to the invention, no such pins are now required, and it is sufficient that the wire loop is bent down over the transplant, as shown in FIGS. 8 and 9, and by means of its stiffness holds the transplant securely against the existing bone tissue 7.

The invention is not limited to the embodiments which are shown by way of example, but instead can be modified within the scope of the patent claims which follow. For example, the wire loops do not necessarily need to be closed, but instead can be open, as has been indicated in FIG. 5, where the wire loop 2 has a free end 19 which is not in contact with the central part 1.

I claim:

1. A device for promoting bone growth used with an implant fixture anchored in a bone tissue, the implant fixture having a bone attaching portion and a flange portion, said device including:

a first part formed as a ring or sleeve sized to be fitted onto the flange portion of the implant fixture; and a second part formed of at least one wire loop having its ends secured to said first part and extending outwardly and at least partly substantially transversely to a longitudinal axis of the first part over a space formed underneath said second part in which bone growth is to be established, said wire loop being made of a biocompatible material which is easily bendable to conform to said space but sufficiently stiff to maintain its shape after being bent.

2. A device for promoting bone growth and adapted for connection to an implant fixture anchored in a bone tissue, the implant fixture being of a specific type having a bone attaching portion and a flange portion protruding from the bone attaching portion, said device comprising:

a central part including means for connecting said central part to the protruding flange portion of the bone-embedded implant fixture, and a peripheral part extending outwardly from said central part and configured to lie above the surrounding bone level over an area where bone growth is sought and defining a free space under the peripheral part for bone ingrowth and also forming a support for one of 1) a flexible, biocompatible membrane of the type which is arranged between soft tissue and the bone tissue, and 2) a bone transplant applied in connection with the implant fixture, said peripheral part including at least one single wire loop extending outwardly from the central part, the wire being made of a biocompatible material and being easily bendable by hand to conform to said area but sufficiently stiff to maintain its shape after bending.

3. A device according to claim 2, wherein said peripheral part forms a supporting base for the membrane and is adapted to maintain said space between the membrane and the bone tissue in order to permit bone growth in said space.

4. A device according to claim 2, wherein said peripheral part is intended to securely hold, during an incorporation process, the bone transplant applied in connection with the implant.

5. A device according to claim 2, wherein said peripheral part consists of two wire loops which extend outwardly in a fan shape from said central part at opposites sides.

6. A device according to claim 5, wherein the two wire loops are asymmetrical, and one wire loop is larger that the other.

7. A device according to claim 5, wherein said wire is made of titanium.

8. A device according to claim 2, wherein the wire is a titanium wire having a thickness of about 0.5 mm.

9. A device according to claim 2, wherein said central part is annular and is arranged, upon insertion onto the implant fixture, to bear against said flange portion of the implant fixture, a lower end surface of said central part having essentially the same external diameter as said flange portion.

10. A device according to claim 9, further including a locking screw for locking said central annular part in the correct position with respect to the implant fixture wherein a head of said locking screw bears against an upper end surface of said annular part, and wherein a threaded part of said locking screw engages with an internal thread of an implant fixture portion.

11. A device according to claim 10, wherein the upper end surface of the annular part comprises two essentially parallel grooves in which the wire loop has been fixed.

* * * * *